US007856365B2

(12) United States Patent
Fiedotin et al.

(10) Patent No.: US 7,856,365 B2
(45) Date of Patent: *Dec. 21, 2010

(54) METHOD AND SYSTEM FOR PROVIDING CURRENT INDUSTRY SPECIFIC DATA TO PHYSICIANS

(75) Inventors: Richard Alan Fiedotin, San Mateo, CA (US); Jeffrey Alan Tangney, Portola Valley, CA (US); Thomas Ho Lee, San Francisco, CA (US)

(73) Assignee: ePocrates, Inc., San Mateo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/332,557

(22) Filed: Dec. 11, 2008

(65) Prior Publication Data

US 2009/0089392 A1  Apr. 2, 2009

(51) Int. Cl.
*G06Q 10/00* (2006.01)
(52) U.S. Cl. ............... 705/2; 705/3; 726/4; 725/81; 707/201; 434/350; 434/322; 434/258; 434/276; 434/262; 348/516
(58) Field of Classification Search .......... 726/4; 725/81; 709/217; 707/201; 705/2, 3; 434/350, 434/322, 306, 276, 262; 348/516
See application file for complete search history.

(56) References Cited

U.S. PATENT DOCUMENTS

| | | | | |
|---|---|---|---|---|
| 4,769,704 A | * | 9/1988 | Hirai et al. ............... 348/516 |
| 5,040,141 A | | 8/1991 | Yazima et al. ............ 364/900 |
| 5,588,009 A | | 12/1996 | Will ......................... 371/33 |
| 5,666,530 A | | 9/1997 | Clark et al. ............... 395/617 |
| 5,737,539 A | * | 4/1998 | Edelson et al. ........... 705/3 |
| 5,757,669 A | | 5/1998 | Christie et al. ........ 364/514.006 |
| 5,777,882 A | | 7/1998 | Salgado ................ 364/478.02 |
| 5,791,907 A | * | 8/1998 | Ramshaw et al. ......... 434/262 |
| 5,810,747 A | | 9/1998 | Brudny et al. ............ 600/595 |
| 5,831,664 A | * | 11/1998 | Wharton et al. ........... 725/81 |
| 5,839,442 A | | 11/1998 | Chiang et al. .......... 128/661.01 |
| 5,845,255 A | * | 12/1998 | Mayaud .................... 705/3 |
| 5,867,821 A | | 2/1999 | Ballantyne et al. ........ 705/2 |

(Continued)

OTHER PUBLICATIONS

EIC search (Jul. 30, 2010).*

(Continued)

*Primary Examiner*—Dilek B Cobanoglu
(74) *Attorney, Agent, or Firm*—Morgan, Lewis & Bockius LLP

(57) ABSTRACT

The present invention provides physicians access to formulary data as well as important clinical and practice management information at the point of care on easy-to-use handheld electronic devices. The invention also provides a method for distributing medical data to medical personnel. The method comprises the steps of storing medical data in a database and periodically communicating selected medical data between the database and an electronic device to establish a medical data distribution system subsidized by sponsoring entities. The invention also provides a computer readable memory storing executable instructions for execution by a computer system such that the computer system functions in a specified manner. The instructions comprise instructions for storing medical data in a database, and instructions for periodically communicating selected medical data between the database and an electronic device to establish a medical data distribution system subsidized by sponsoring entities.

30 Claims, 7 Drawing Sheets

U.S. PATENT DOCUMENTS

| | | | | |
|---|---|---|---|---|
| 5,868,669 | A | | 2/1999 | Iliff .............................. 600/300 |
| 5,875,178 | A | | 2/1999 | Rahuel et al. ................ 370/313 |
| 5,884,325 | A | * | 3/1999 | Bauer et al. ................... 707/201 |
| 5,951,638 | A | | 9/1999 | Hoss et al. ................... 709/206 |
| 5,958,005 | A | | 9/1999 | Thorne et al. ............... 709/202 |
| 5,961,590 | A | | 10/1999 | Mendez et al. .............. 709/206 |
| 5,999,932 | A | | 12/1999 | Paul ............................ 707/10 |
| 6,039,575 | A | * | 3/2000 | L'Allier et al. .............. 434/323 |
| 6,076,166 | A | * | 6/2000 | Moshfeghi et al. .............. 726/4 |
| 6,149,440 | A | * | 11/2000 | Clark et al. .................. 434/322 |
| 6,162,060 | A | | 12/2000 | Richard et al. .............. 434/118 |
| 6,199,106 | B1 | * | 3/2001 | Shaw et al. .................. 709/217 |
| 6,249,809 | B1 | * | 6/2001 | Bro .............................. 709/217 |
| 6,256,613 | B1 | * | 7/2001 | Falchuk et al. .................. 705/2 |
| 6,261,103 | B1 | * | 7/2001 | Stephens et al. ............. 434/276 |
| 6,275,850 | B1 | | 8/2001 | Beyda et al. ................. 709/206 |
| 6,282,404 | B1 | * | 8/2001 | Linton ......................... 434/350 |
| 6,305,377 | B1 | | 10/2001 | Portwood et al. ............ 128/897 |
| 6,475,146 | B1 | | 11/2002 | Frelburger et al. ........... 600/437 |
| 6,493,007 | B1 | | 12/2002 | Pang ........................... 345/835 |
| 6,546,230 | B1 | | 4/2003 | Allison ........................ 434/350 |
| 6,807,254 | B1 | | 10/2004 | Guedalia et al. ........... 379/88.1 |
| 6,910,068 | B2 | | 6/2005 | Zintel et al. ................. 709/220 |
| 6,993,531 | B1 | | 1/2006 | Naas ........................... 707/102 |
| 7,149,770 | B1 | | 12/2006 | Kalva et al. ................. 709/203 |
| 2001/0016310 | A1 | * | 8/2001 | Brown et al. ................ 434/306 |
| 2002/0035484 | A1 | | 3/2002 | McCormick .................... 705/2 |

OTHER PUBLICATIONS

Anonymous, *A Windows CE Virtual Charting Application*, Health Management Technology, Dec. 1996, 17(13):26-27.

Anonymous, Dialog 16 (Gale Group PROMT(R)), No. 06836488, *New ePocrates Software Will Help Prevent Accidents with Prescription Medication; Medication Mistakes Cause an Estimated 7,000 Deaths Annually*, Business Wire, Dec. 1, 1999, 2 pages.

Anonymous, *Electronic Point-of-Care Prescribing: Selling the Benefits, Identifying Initial Steps for Success*, Formulary Jan. 1999, 34(1):68-69.

Anonymous, *Medical Technology Start-Up Provides Medical Professionals with Mobile Point of Care Automation*, Business Wire, Jul. 19, 1999, 2 pages.

Anonymous, *ParkStone Introduces New Hand-Held, Electronic Point-of-Care Tool Based on Microsoft Windows CE for Physician Efficiency and Improved Patient Care*, PR Newswire, Jul. 12, 1999, 3 pages.

Bennahum D, *Docs for Docs*, Wired Digital, Inc., 1994-2003 (http://www.wired.com/wired/archive/3.03/medisys_pr.html).

Carlson J, *Turning on the Cyberphysician*, Medical Marketing and Media, May 1997, 32(5):50-60.

Castagnoli W, *Whittle's Medical New Network, Making Waves in Rx Marketing*, Medical Marketing and Media, Jun. 1993, 28(6):14(5).

Kelly R, *US Health Link-An Online Information Service for Health Professionals*, Journal of Family Practice, TCG Health&Wellness DB, May 1993, 36(5):572(2).

Menduno M, *Apothecary.now*, Hospitals & Health Networks, Jul. 1999, 73(7):34-40.

Parker G, *Easing Workflow in the Palm of Physicians' Hands*, Health Management Technology, Nov. 1999, 20(10):48-49.

Screenshots from Microsoft Windows CE-1.00 Pegasus (XP7901515), 4 pages.

Tanenbaum S, Excerpt from "Computer Networks" 3rd Edition, published 1996 (XP7901514), 5 pgs.

* cited by examiner

FIG. 3M — Accupril / quinapril
Serious Reactions
hyperkalemia
myocardial infraction
exfoliative dermatitus
agranulocytosis
hepatotoxicity Common Reactions
dizziness
headache
▲ Adverse Reactions [Back][Home]

FIG. 3N — Accupril / quinapril
Contraindications/Cautions
hypersensitivity to drug
history of angioedema
pregnancy
caution if impaired renal fxn
caution if hyperkalemia
▲ Contraind/Caut. [Back][Home]

FIG. 3O — Accupril / quinapril
Drug-Drug Interactions
diuretics
K sparing diuretics
K supplementation
lithium
tetracycline
▲ Drug Interactions [Back][Home]

FIG. 3P — Accupril / quinapril
Cigna
Y: Approved

Co-Pay
Lowest co-pays for this plan are at
yourPharmacy.com
1-800-363-DRUG

Average Wholesale Prices
Strength: 20 mg
▲ Cost Summary [Back][Home]

FIG. 3Q — Accupril / quinapril
Lowest co-pays for this plan are at
yourPharmacy.com
1-800-363-DRUG Average Wholesale Prices
Strength: 20 mg
Quantity: 90   Price: $88.05

Strength: 40 mg
Quantity: 90   Price: $88.05
▲ Cost Summary [Back][Home]

FIG. 3R — Accupril / quinapril
Pregnancy: D
Lactation: ?
Metabolism: liver, partially
Excretion: urine, primary
DEA: not controlled Mfgr: Parke-Davis
Class: ACE-I/A2R-Antagonists Cigna formulary last updated Oct 1,
▲ Other Info [Back][Home]

FIG. 3S — Accupril
D: Human studies demonstrate risk but may need to weigh risk/benefit in life-threatening situations
Metabolism: liver, partially
Excretion: urine, primary
DEA: not controlled Mfgr: Parke-Davis
Class: ACE-I/A2R-Antagonists Cigna formulary last updated Oct 1,
▲ Other Info [Back][Home]

FIG. 3T — Accupril
?: Safety is unknown; should be given with caution; controversial
Lactation: ?
Metabolism: liver, partially
Excretion: urine, primarily
DEA: not controlled Mfgr: Parke-Davis
Class: ACE-I/A2R-Antagonists Cigna formulary last updated Oct 1,
▲ Other Info [Back][Home]

FIG. 3U — Accupril
not controlled: Drug is not subject to the Controlled Substances Act of 1970
Metabolism: liver, partially
Excretion: urine, primarily
DEA: not controlled Mfgr: Parke-Davis
Class: ACE-I/A2R-Antagonists Cigna formulary last updated Oct 1,
▲ Other Info [Back][Home]

FIG. 3V — Accupril / quinapril
(notes lines)
▲ Notes [Back][Home]

FIG. W — Edit Categories
Edit Categories
Enter a new category name:
MyDrugs
[OK] [Cancel]

FIG. 3X — Edit Categories
MyDrugs
[OK] [New] [Rename] [Delete]

| Accupril | | Drug \| Edit \| Options | | Drugs ▼MyDrugs |
|---|---|---|---|---|
| quinapril | | Categorize... ✓T | | Maxicare |
| Serious Reactions | | Beam Note | | Accupril Y |
| hyperkalemia | | Beam All Notes | | Meridia Y |
| myocardial infraction | | myocardial infarction | | Ritalin Y |
| exfoliative dermatitis | | exfoliative dermatitis | | |
| agranulocytosis | | agranulocytosis | | |
| hepatotoxicity | | hepatotoxicity | | |
| Category Select | | Common Reactions | | |
| Category: MyDrugs | | dizziness | | |
| Unfiled | | headache | | |
| OK \| Edit Categories... | | ▲Adverse Reactions (Back)(Home) | | Look Up:......(By Class)(Home) |

FIG. 3Y     FIG. 3Z     FIG. 3AA

| Disclaimer | Drug Edit \| Options | About ePocrates |
|---|---|---|
| Medical Database Disclaimer: User acknowledges and agrees that (a) ePocrates may, from time to time, elect to update information contained in the Database, but ePocrates does not warrant or guarantee that any product description(s) or other information contained in the Database or accessed through the Software will | quinapril Abbreviations... ✓A (5,10,20,40) Prefeences... ✓R Health Net ( Disclaimer... Y: Approved About ePocrates hypertension [20-80 mg PO qd/bid] Start: 10 mg PO qd; Max: 80 mg/d; Info: adjust q2wks, adjust dose if renal dysfxn | ePOCRATES ePocrates qRx Pro 2.0 Please send comments or suggestions to feedback@epocrates.com (c) ePocrates, Inc. 1999 |
| OK | ▲Dosing Summary (Back)(Home) | OK (Credits) |

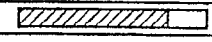

METHOD AND SYSTEM FOR PROVIDING CURRENT INDUSTRY SPECIFIC DATA TO PHYSICIANS

This application claims priority to U.S. patent application Ser. No. 09/487,932, filed Jan. 20, 2000, which is incorporated fully herein by reference.

TECHNICAL FIELD

The present invention relates to a system and method for delivering industry specific data to professionals and in particular to providing physicians with access to current health care industry information.

BACKGROUND

The health care industry is an extraordinarily large and information intensive sector of the United State's economy. Many different participants in the health care industry constantly rely on a vast amount of data-intensive information. Physicians, for example, rely on information to make decisions which influence a disproportionately large portion of all spending in the health care sector. Over the years, a robust health care information system (HIS) industry has developed, in part to provide physicians with the data they need to make informed-decisions. Despite the growth of the health care sector in general and the HIS industry in particular, an information system infrastructure which satisfies the needs and wants of physicians has not yet been developed.

Numerous problems exist with today's health care information systems. A few of the more important parties will now be examined in terms of the problems they are facing.

Health Care Insurance

Health care insurance is an enormous industry, typically focused on generating revenue through increased contracts and by controlling costs through the management of claims reimbursement. One of the larger components of the insurance cost structure is derived from prescription medication, the cost of which rises significantly each year. The majority of the insurance industry has attempted to lower these costs by outsourcing the management of prescription medication reimbursement to intermediaries known as Pharmacy Benefit Management organizations (PBMs).

PBMs are companies who track all prescriptions written by physicians in a health plan the physician has contracted with. They administer prescription drug claims, establish formularies, track physician prescribing patterns, provide education to improve their efficiency and cost effectiveness, and provide disease management programs. The main function of PBMs, however, is to control the cost of prescription drugs.

To lower costs of prescription drugs, PBMs negotiate prices on medications with pharmaceutical companies. They then attempt to determine the price-performance profile of all the drugs on the market. As different pharmaceutical companies negotiate different prices, these profiles will vary according to payer. At the end of this evaluation, the PBMs create a "formulary" which is a list of medications that the PBM will cover. A formulary may contain either brand name drugs or generic drugs. Generic drugs have the same active ingredients, strength, and dosage form and are therapeutically equivalent to their brand-name counterparts. Many health plans revise their formulary lists frequently, resulting in changes that the patient and his or her physician may not be aware of. Patients often learn of the change only when their pharmacist informs them, or when they collect their prescription medication and notice a difference, which leaves insufficient time to appeal the change. Some health plans provide physicians with a monthly drug budget, financially penalizing physicians if they go over budget and rewarding them if they stay below budget. This is commonly referred to as "risk sharing" or "risk pooling". Most medication on the market has a status within the formulary. The status of any medication may therefore be preferred, approved, approved with prior authorization by the payer, available only as a generic, or not approved. Medications that are on-formulary have therefore been approved by a particular health plan, and medications that are off formulary have not been approved.

The PBMs communicate this formulary to physicians by mailing them binders containing formulary information every three to six months. Each health plan has its own formulary so a physician may receive as many as 100 different booklets, though 20-30 is more typical. The content of the formulary is reinforced by a PBM "detail" force of PBM representatives who visit the physician periodically. Despite the above, physicians typically have a low compliance with these formularies.

PBMs typically enforce the formulary at the pharmacy. When a patient submits a prescription, the pharmacist enters an on-line system which checks the medication against a specific health plan's formulary. If the medication is on-formulary, it is dispensed, generally with a co-payment by the patient. If it is off-formulary and a generic substitute has not been authorized, the patient either pays for the medication himself or the pharmacist calls the doctor's office to request an alternative. This process can be time consuming, requiring the patient to either wait in the pharmacy or return at a later time.

PBMs exist to manage and enforce these formularies. PBMs are therefore constantly seeking ways to increase physician compliance without incurring significant financial and/or political costs. Mailing the binders and using detail forces are costly. Rejecting prescriptions at the pharmacy level generates significant animosity among the physician community and does little to encourage higher compliance with the formularies. Prescribing off-formulary medication and the lack of communication between PBM's and physicians results in higher transaction costs for the patient.

PBMs, consequently, need a solution at the point-of-care to help reduce their cost of operations and minimize the burden their formularies impose on physicians and patients.

Furthermore, patients referred to specialists by physicians, can often only see specialists specific to their particular health plan. Physicians typically have difficulty in determining which specialists are on a particular health plan, particularly specialists in the patients' geographical area.

Some health plans also incorporate an exacting list of billing codes for different medical procedures. When submitting a claim on behalf of a patient, a physician will typically need to submit these codes in order to be paid. Some physicians have prepared a form listing the more common procedures, next to which they can check a box, to facilitate the task of submitting claims. Unfortunately not all types of procedures can be listed, which leads to the physician checking a box which is closest to the completed procedure. This leads to inaccuracies and non compliance with the specific health plans rules. The most common systems of billing codes are ICD9, CPT4 and E&M. ICD9 is an international classification of disease that assigns a unique number to each different diagnosis. CPT4 codes are procedure codes, so for example, a left main artery bypass would have a certain code associated with it. E&M codes are similar to CPT4 codes. Presently physicians use a form called a "superbill" which lists approximately 90 different codes (charge capture). As there are thousands of codes, and only so many on the superbill, a physician tends to be non-specific when completing the form. If more specificity could be provided, physicians may be able to charge more accurately.

Certain health plans have also adopted specific clinical protocols that physicians contracted to the plan must follow. There are typically vast amounts of clinical protocols contained in books which the physician does not always have the time to consult. A technical solution at the point-of-care could alleviate this problem.

Physicians

Physicians are under increasing pressure to see more patients per day. Moreover, they are subject to an ever-increasing number of rules which require a significant amount of time to comply with.

The above-mentioned formulary represents one of these restrictions. Currently, physicians have one copy of each formulary for each health plan with which their practice contracts. Typically, a high-volume physician will contract with 20-30 plans, depending on the region in which he works, so there will be 20-30 formulary booklets in a common area of his or her office. It is simply impossible for the physician to remember which medications are on which plans. Consequently, when a physician writes a prescription, he has two choices. He can leave the patient in the exam room for about two minutes while he looks up the formulary status of the drug he wishes to use and select an alternative if necessary or he can simply prescribe without knowing the medication's formulary status. In the latter scenario, there is a significant chance that the medication will be off-formulary and his office will receive a call from the pharmacy. The staff will have to pull the patient's chart at an additional cost and ask the physicians to authorize the substitution. The patient, meanwhile, must wait at the pharmacy until the substitution is made. If the physician's compliance rate is low enough and he operates under a risk sharing contract with the insurance company for pharmaceutical costs, failure to comply can actually carry a direct financial penalty. In either scenario, the physician has spent a fair amount of time complying with insurance rules and not treating patients. It is estimated that as much as 20% of all prescriptions are still written off-formulary.

The problem of complying with formularies has grown worse in recent years due to the proliferation of contracted health plans and the fact that formularies are becoming increasingly restrictive.

The problem physicians face with formularies can be extended to the higher order problem they face of inadequate access to information in general. This problem is well-known and ranges from missing charts to inaccessible lab reports and unknown medical records. The results are increased incidence of disease and mortality, higher costs, and wasted resources. Recent studies show that approximately 100 000 deaths a year occur due to medication errors. Physicians may also have poor access to up-to-date clinical information and/or drug prices. Clinical information may include pharmacopeia which describes drugs, chemicals, and medicinal preparations and is typically issued by officially recognized authorities to serve as a standard. Furthermore, the Food and Drug Administration (FDA) has introduced a faster process for approving drugs, leading to a increase in the number of drugs available each year.

Information technology has been employed to address these problems with limited success. A problem encountered has been getting the physician, the key decision-maker, to use such technologies.

Every day, hundreds of thousands of physicians treat millions of patients using a combination of experience, judgment and data. When this data is missing or inadequate, treatment is impaired. The impact, which depends on the nature of the information and the condition of the patient, can for example include: patients suffering complications, including death, from contraindicated medications; doctors spending significant time looking for information and making inappropriate clinical decisions when on call; and insurers incurring the cost of extra nights of expensive hospitalization due to "missing" lab results.

The applications developed for physicians to date have been excessively ambitious, requiring the doctor to change his or her practice patterns to conform to new technology. Such applications have also been cumbersome, inefficient, and rigid, slowing the physician down at a time when he or she is being forced to see more patients per hour. Moreover, most applications have been designed for desktop or tablet computers. This fails to recognize that physicians are not deskbound and do not have wireless systems in their offices. The inadequacies of these applications and their hardware platforms has restricted their use by physicians which, in turn, has prevented the population of clinical databases which could be used for clinical decision support.

Access to electronic databases containing medical information has typically been a complicated process at an added expense to the physician, a cost which is ultimately passed on to the patient.

Furthermore, physicians have typically not obtained much training in the areas of business and practice management. Information and advice in these areas would therefore be appreciated by many practicing physicians.

Pharmaceutical Companies

A large portion of pharmaceutical companies revenues are derived from prescriptions written by physicians. Physicians who prescribe more medication are of heightened interest to the pharmaceutical industry because they generate a disproportionately large percentage of a pharmaceutical company's revenue.

As industry revenues have grown, so has the proliferation of new products. While there has been much innovation, many of these new medications are little different from other drugs in the same therapeutic category. The pharmaceutical industry is highly leveraged operationally. Most research and development expenditures are fixed and sunk. Manufacturing, however, has minimal fixed costs. The result is that pharmaceutical companies operate with large gross margins and therefore any incremental sale affects their profits. The result is an intense pressure to increase sales and to capture market share. Consequently, pharmaceutical companies spend an extraordinary amount of money on marketing, particularly to physicians, to accentuate the minimal differences between medications.

In health care, the end user has little influence on the purchasing decision and drug selection remains to a large extent the choice of the physician. Consequently, pharmaceutical companies spend an inordinate amount of money trying to influence the behavior of physicians. Pharmaceutical sales forces comprise a large component of this spending. The problem for pharmaceutical companies is that their sales forces are not able to spend as much time with the high-value, top percentage of physicians as they would like; instead they visit less valuable physicians who have fewer pharmaceutical company representatives calling on them and more time to spend with each. Pharmaceutical companies therefore need a means for giving their representatives access to these high-value physicians.

Furthermore, insurance companies create a barrier for the pharmaceutical companies through their formularies. These lists of approved medications are extremely difficult to memorize. Often, given the similarity between drugs of a therapeutic class, physicians simply prescribe the drug which appears to be on most formularies to minimize the chance of their guess being incorrect.

In addition, pharmaceutical companies typically also have a poor and ineffective Internet presence which does not attract physicians to their Web sites to, for example, familiarize themselves with current developments.

Contract Research Organizations

Contract Research Organizations (CROs) conduct clinical trials on new and existing medications and devices to gain more information about them. Development of new drugs is a long and complex process. Prior to any exposure to humans, a drug must be shown to be safe and non-toxic in extensive animal studies. Once this safety is proven, the drug is first given to normal, healthy volunteers (Phase I trials). Once safety is shown in healthy volunteers, the drug is given to patients with the specific medical conditions that the drug was designed to treat (Phase II & III studies). If the drug appears safe and effective, then application is made to the regulatory authorities to grant approval to market the medication to the public. Often, once the medication is on the market, additional studies are performed. These studies are called Phase IV studies.

CROs often have difficulty acquiring principal investigators (Medical Doctors) to undertake clinical trials of new drugs on their patients for Phases I to IV. Furthermore Contract Research Organizations may have difficulty enrolling patients into their clinical trials.

A technology that could help alleviate these problems would accelerate drug approval and ultimately lower drug costs.

Managed Care Organizations

A managed care organization is a health care provider (or group of medical service providers) who contracts to provide a wide variety of healthcare services to enrolled members through participating providers. These organizations typically do not have a means of communicating with physicians to, for example, inform them of changes in the industry. Managed Care Organizations also have difficulty enforcing compliance with their rules and regulations.

A widespread means of communicating with physicians and assisting their compliance with the rules could reduce overall health care costs.

Healthcare Information Systems Developers

Healthcare information systems companies (HIS) sell complex solutions to the health care industry. Some of their applications are for nurses, others for administrators, and still others for physicians. Physicians are particularly influential, even though they do not use these applications as much as others, and applications supplied to physicians are currently not widespread. The various platforms which currently exist for supplying physicians with different types of information do not aggregate a multitude of healthcare information. In order to access a large number of healthcare professionals, healthcare information developers need to sell their product to an Integrated Delivery Network of doctors, hospitals and clinics (IDNs). There is no current effective means for supplying these applications directly to physicians on a wide scale basis.

Medical Web Sites

Another means of supplying physicians with healthcare information is via healthcare dedicated Web sites on the Internet. Typically however such sites experience low Web traffic with physicians. Studies have shown that non-medical Web sites also experience low Web traffic with valuable physicians.

The present invention attempts to address the above-mentioned problems which have not significantly been dealt with by the health care or information technology industries.

American Medical Association

The American Medical Association's ethical opinion 8.061 deals with "Gifts to Physicians from Industry". Many gifts given to physicians by companies in the pharmaceutical, device, and medical equipment industries serve an important and socially beneficial function. However, any gifts accepted by physicians individually should primarily entail a benefit to patients and should not be of substantial value. Accordingly, textbooks, modest meals, and other gifts are appropriate if they serve a genuine educational function. Furthermore, no gifts should be accepted if there are strings attached. For example, physicians should not accept gifts if they are given in relation to the physician's prescribing practices. Therefore gifts which influence a physician's prescribing practices may be unethical. A need therefore exists for an outside party, not dictated to by industry, to supply up-to-date information to physicians.

In order for new technology to be accepted by physicians, the technology utilized should be mobile, intuitive, and fast, with little or no training required. The system should fit the physician's workflow and not require physicians to leave the examination room or otherwise disrupt their interaction with patients. There should be little or no data entry required, simple point-and-click navigation, rapid response times, and one-touch "transparent" data updates from Web-accessible desktops. The invention should improve patient care, be easy for the physician to use, and be provided to the physician at no expense. It should also influence the existing and developing infrastructure and include the major industry participants in order to accelerate implementation and gain support.

SUMMARY OF THE INVENTION

The present invention addresses the above-mentioned problems by providing physicians access to important clinical and practice management information at the point of care on easy-to-use handheld electronic devices. The invention uses a handheld computing platform to provide information such as formulary status, dosing, co-payments, drug interactions, and adverse reactions. This information resides on the handheld computer itself and is preferably updated through a transparent connection process to the Internet via a desktop computer.

The applications on the handheld computer are intuitive and easy to use, with minimal disruption to physician's practice patterns. The applications are designed primarily, though not exclusively, to provide the physician access to information when he or she is away from the source (i.e. on call or at home).

According to the invention there is provided a method for distributing medical data to medical personnel. The method comprises the steps of storing medical data in a database and periodically communicating selected medical data between the database and an electronic device to establish a medical data distribution system subsidized by sponsoring entities. Sponsorship rights are sold to sponsoring entities, where the sponsorship rights at least partly fund the medical data distribution system. The sponsoring entities are preferably selected from a group consisting of pharmaceutical companies, pharmacy benefit management organizations, health care insurers, pharmacies, medical suppliers, medical publishers, contract research organizations or managed care organizations.

The electronic device is preferably a handheld computing device and is distributed preferably at no cost (or at a discount) to medical personnel, such as physicians, where the handheld computing device is subsidized by the sponsoring entities.

According to the invention there is further provided a computer readable memory storing executable instructions for execution by a computer system such that the computer system functions in a specified manner. The instructions comprise instructions for storing medical data in a database, and instructions for periodically communicating selected medical data between the database and an electronic device to establish a medical data distribution system subsidized by sponsoring entities. The present invention also provides a computer readable memory storing executable instructions for execution by a handheld computer system such that the handheld computer system functions in a specified manner. The instructions comprising instructions for accessing a list of health care insurance plans, where each of the health care insurance plans include an associated formulary list, and instructions for automatically determining and displaying the status of a particular pharmaceutical relative to a particular health care insurance plan's formulary list.

Finally according to the invention there is provided an information management system for delivering data to physicians. The system comprises a data processor, a communication interface for communicating with at least one handheld computing device, where the communication interface is coupled to the data processor, a database of aggregated pharmacopeia and formulary information further coupled to the data processor, and a memory coupled to the data processor for storing instructions for execution by the data processor. The stored instructions comprise instructions for storing medical data in a database, and instructions for periodically communicating selected medical data between the database and an electronic device to establish a medical data distribution system subsidized by sponsoring entities.

BRIEF DESCRIPTION OF THE DRAWINGS

The foregoing and additional features and advantages of the present invention will be more readily apparent from the following detailed description, which proceeds with reference to the accompanying drawings.

DETAILED DESCRIPTION OF PREFERRED EMBODIMENTS

Health Care Information

Figure 1:
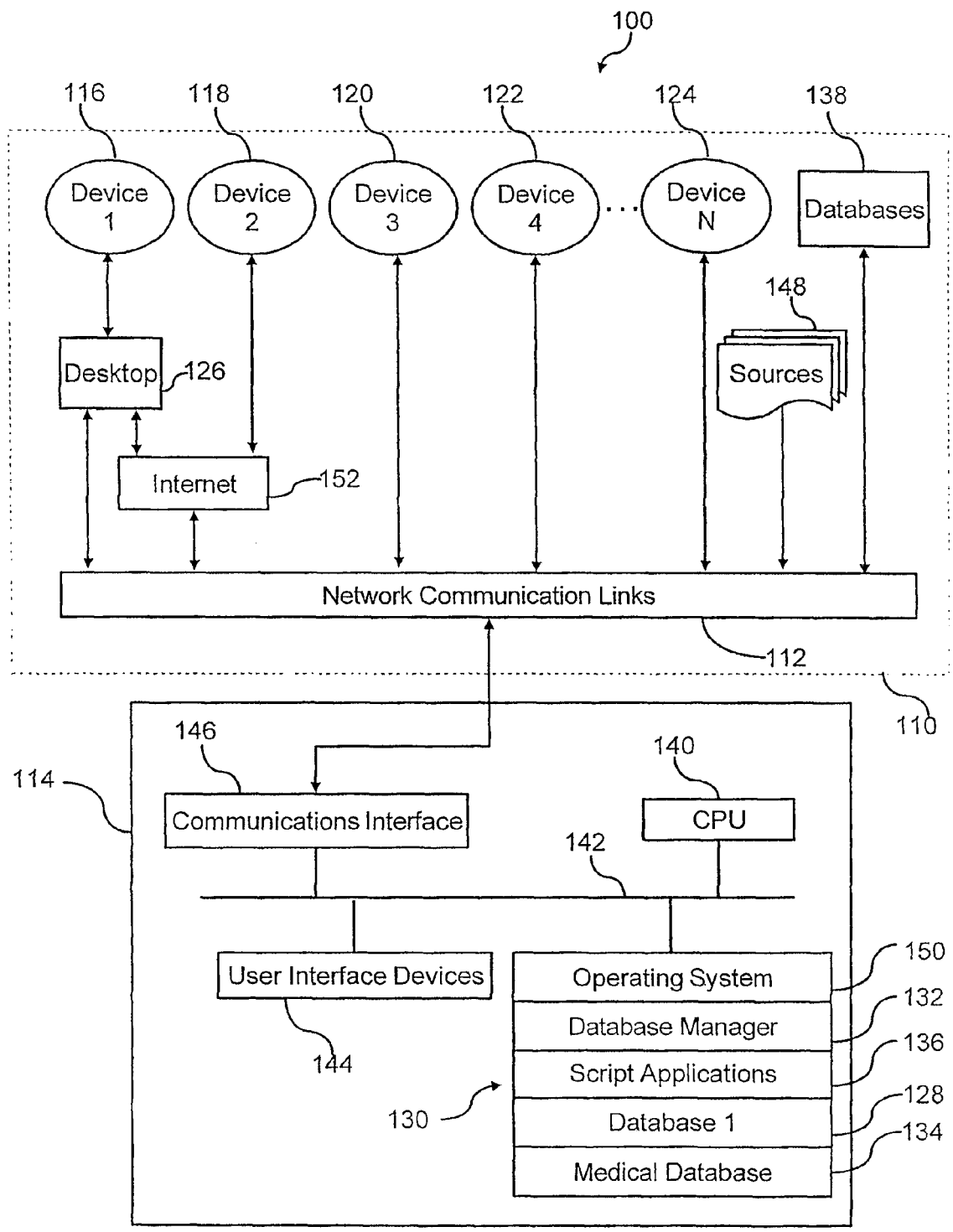
FIG. 1 is an information management system according to a preferred embodiment of the present invention.

The present invention attempts to address some of the difficulties experienced by patients, doctors, and the health care industry as a whole FIG. 1 illustrates an information management system 100 according to a preferred embodiment of the present invention. The information management system 100 includes a communication network 110 covering a wide coverage area, preferably the entire globe. The communication network 110 comprises a series of points or nodes interconnected by communication paths. The network can interconnect with other networks, contain subnetworks and may be characterized in terms of its spatial distance as either a local area network (LAN), metropolitan area network (MAN), or wide area network (WAN). The network may further be characterized by the type of data transmission technology in use on it (for example, a TCP/IP (Transmission Control Protocol/Internet Protocol) or SNA (Systems Network Architecture) network); by whether it carries voice, data, or both kinds of signals; by who can use the network (public or private); and by the usual nature of its connections (dial-up or switched, dedicated or nonswitched, or virtual connections). By using sharing and exchange arrangements with other organizations, the communication network 110 may also make use of large telephone infrastructures to access larger networks (such as the Internet 152). The communication network 110 may therefore for example be an Internet-based network or a private Intranet based network. The communication network 110 may also use a combination of network communication links 112, such as for example coaxial cable, copper wire, optical fiber, wireless, microwave or satellite links. The communication network 110 connects at least one server 114 via the communication links 112, to a plurality of electronic devices 116-124. The electronic devices 116-124 preferably comprise handheld computing devices or Personal Digital Assistants (PDAs). In the preferred embodiment the server 114 may also link to other electronic devices such as desktop computers 126 which may in turn connect to the handheld computing devices 116-124.

Server 114 comprises a central processing unit (CPU) or data processor 140, a memory 130, user interface devices 144, a communications interface circuit 146 and a bus 142 that interconnects these elements. At least one database 128 is located within a memory 130. The database 128 contains a collection of data organized so that its contents can easily be accessed, managed, and updated. The database 128 may for example comprise a relational database (a tabular database in which data is defined so that it can be reorganized and accessed in a number of different ways), a distributed database (that can be dispersed or replicated among different points in a network), or an object-oriented database (that is congruent with the data defined in object classes and subclasses). Furthermore there is provided a medical database 134 containing aggregated medical or health care data or files. Such aggregated data may include formularies, clinical data, pharmacopeia type information, clinical information, formularies, dosing information, co-payment information, drug pricing, adverse reaction information, drug-drug reaction information, contra-indication information, metabolism or excretion information, Drug Enforcement Agency schedules, drug trial information or criteria, lab results, pathology reports, x-ray reports, medical records, reference data, billing codes, electronic prescription information, charge capture information, pregnancy information, or lactation information. A database manager 132 provides the capability of controlling read/write access, specifying report generation, and analyzing usage. Data may be entered into the database manually via user interface devices 144 or existing data may be converted and stored in the database using script applications 136. Server 114 runs on an operating system 150 contained within memory 130. The operating system may store instructions for aggregating data, communicating storing data, searching the data, etc. Server 114, connects to the communication network 110 and may also access other databases 138 via network communication links 112.

The PDAs 116-124 comprise any small mobile hand-held device that provides computing and/or information storage and retrieval capabilities for personal or business use. Many people use the name of one of the popular PDA products as a generic term, such as Hewlett-Packard's Palmtop® or 3Com's Palm V™ Connected Organizer. Most PDAs have a small keyboard while others have an electronically sensitive pad or touchscreen on which handwriting can be received. Typical uses include schedule and address book storage and retrieval and note-taking. Some PDAs are combined with telephones, paging systems or wireless networks. PDAs typically use either a variation of the Microsoft Windows® operating system called Windows CE® or other proprietary operating systems, such as the Palm OS®.

Health care data is compiled from various sources 148, such as for example other clinical databases, other networks including the Internet or other heath care industry company's Intranets.

Data may include, but is not limited to, pharmacopeia type information, clinical information, formularies, dosing information, co-payment information, drug pricing, adverse reaction information, drug-drug reaction information, contra-indication information, metabolism/excretion information, Drug Enforcement Agency schedules, drug trial information or criteria, lab results, pathology reports, x-ray reports, abridged medical records, reference data, billing codes, clinical protocols and pregnancy and lactation information. Using the server 114, the various sources 148 of data are aggregated and stored in database 128. According to the invention the data aggregated from various sources 148 and stored within the database 128, is transmitted to the PDAs 116-124 either directly, via the Internet 152 or via a desktop computer 126. The desktop computer 126 may in turn connect to the server 114 via the network communication links 112.

To understand how the server 114 transmits data to the PDAs 116-124, one needs to examine the preferred data transfer mechanism.

Figure 2:
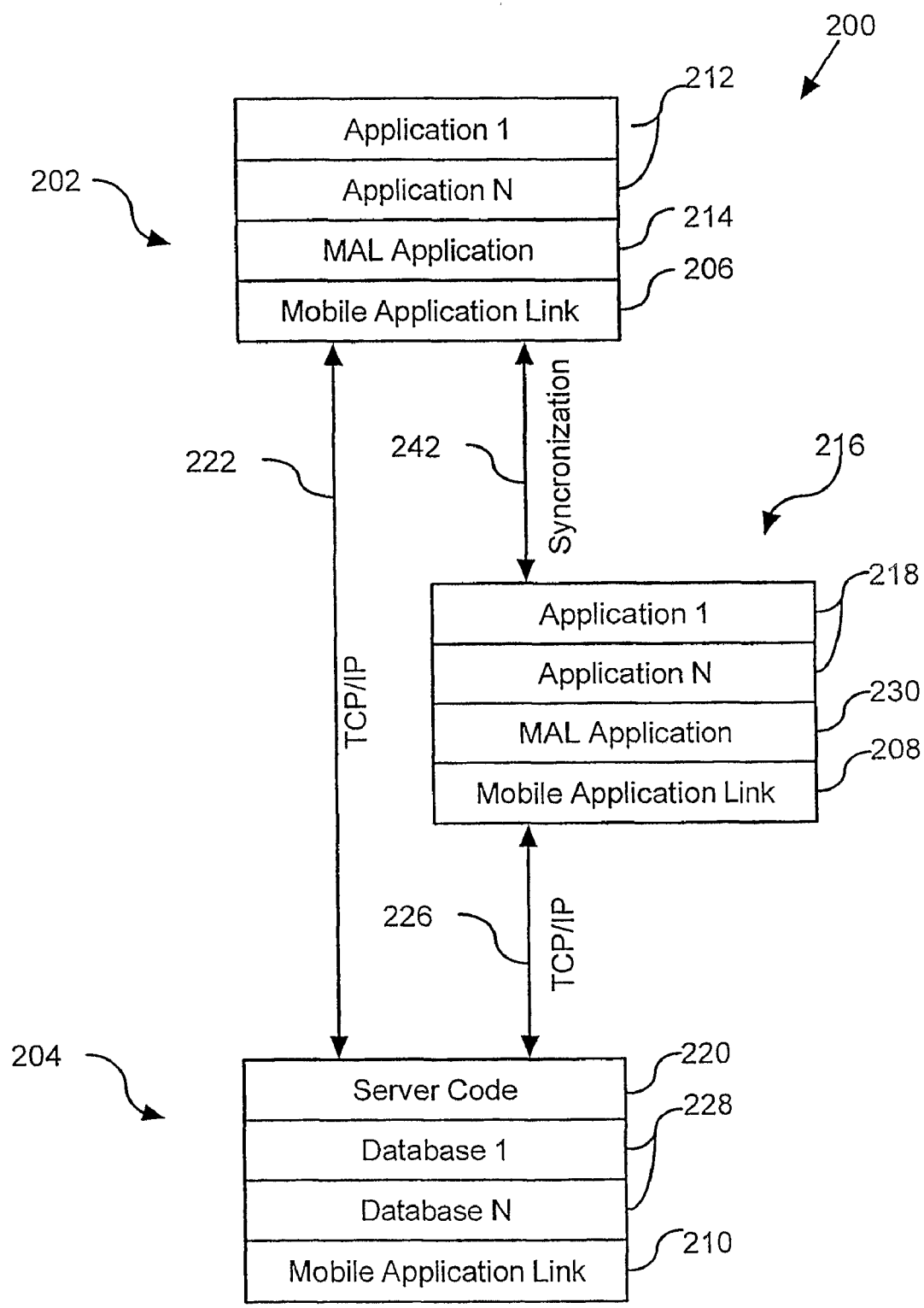
FIG. 2 illustrates a schematic of a data aggregation system according to a preferred embodiment of the present invention.

FIG. 2 illustrates a system 200 for enabling applications on PDAs 202 to interact with data that is managed by a server 204. AvantoGo Inc. has released the Mobile Application Link (MAL) as open source under the Mozilla public license agreement. The MAL technology, includes source code, APIs (application program interfaces) and transfer protocols. Mobile Application Link (MAL) is communication software that allows PDAs 202 to synchronize data with centralized application servers. Currently, MAL works with all Microsoft Windows CE® devices and Palm OS® devices.

Typically, one synchronizes the contents of a PDA 202 with similar contents on a desktop computer 216. To do this, one connects the PDA 202 directly to a desktop computer 216, and an ActiveSync® or HotSync® operation transfers data between the two devices. ActiveSync® or HotSync® are proprietary applications which synchronize PDA applications 212 with similar applications on a desktop computer 216. Some PDA applications 212 synchronize with a centralized server 204 accessible on the Internet or on a corporate Intranet instead of synchronizing data to the desktop computer 216. The centralized server might store HTML (Hypertext Markup Language) files retrieved from the Internet, phone lists that a particular company uses, PDA-side applications to be downloaded, or other data that is shared among groups of people. MAL provides a common and convenient way for these servers 204 to communicate with a user's desktop computer 216 and PDA 202. A MAL client on a desktop computer 216 and on a PDA 202 can synchronize with any server 204 that is MAL compliant.

MAL has components that reside on the PDA 202, on the desktop computer 216, and on the server 204. On the PDA 202, MAL is a library 206 that applications 212 on the PDA 202 can access and use. This library 206 knows how to construct a MAL protocol message and does so when the user performs a synchronizing operation using a communication link 242 attached to the PDA 202. Also on the PDA 202 is a MAL application 214 that is used to configure which servers the MAL library can access. On the desktop computer 216, MAL is a conduit 208 that constructs MAL messages when the user synchronizes the PDA 202 with the desktop computer 216. A conduit is a module that provides a translation bridge between a PDA application 212 and a particular desktop application 218. During the synchronization, this conduit connects to the remote server and communicates with it using the MAL protocol. The conduit synchronizes and/or backs up data between applications on the desktop 218 and the applications on the PDA 212. The conduit may also be used to install new PDA applications 212 that have been stored on the desktop computer 216. The conduit may communicate via direct cable connection, modem connection, or via other network connections. A synchronization manager application (not shown) oversees the process of synchronizing the PDA 206 with the desktop computer 216.

Also on the desktop 216 is a MAL application 230 similar to the application 214 on the PDA 202. Application 230 is used to configure which servers the MAL conduit can access. On the server 204, MAL is built-in to the server code 220. The MAL-compliant server knows how to receive and parse MAL messages and how to construct a MAL message as a response. Each of these components is a necessary part of the MAL architecture. The PDA 202 can connect to the server directly, for example via the Internet, or via the desktop computer 216. The desktop computer 216 may in turn connect to the server, for example via the Internet. From the server's point of view, these two connections are no different from one another. The server simply waits to receive MAL messages from a PDA and does not distinguish how that PDA connected to it.

The server 204 using MAL, may therefore synchronize data contained within its databases 228 with a PDA 202 directly or via the desktop 216. The server connection to the PDA or desktop is preferably via a TCP/IP connection 222, 226.

It should be emphasized that MAL is only one way of transmitting data between a server 204 and a PDA 202, other methods may also be used.

Each PDA may also contain a number of databases (not shown). These may include a formulary database, a medical classes database, strings databases, a names database, a clinical database and a utilities database. The formulary database contains formulary data; the medical classes database contains a list of all the medical classes and the higher relationship between the medical classes and the types of drugs used for treatment within those classes; and the names database contains a list of all the drug names. The clinical database contains clinical data and the utilities database contains miscellaneous data. Multiple strings databases contain string pools for the text displayed in the various Graphical User Interfaces (GUIs) of the PDA.

Another type of database that may be present on the PDA is a tracking or audit database. Every screen, click or stroke made on the PDA and the time spent on any GUI, may be recorded in the tracking database. Every time a user accesses a GUI a count is incremented and written to the tracking database as count data. Also every time a user accesses a GUI all inputs, such as for example keystrokes, may also be recorded. When the PDA is synchronized with the server, all data within the tracking database may be uploaded to the server and stored. The count and input data stored on the server may be used in a number of ways. For example, the count may be used to observe how often and for how long a physician is accessing the formulary database. Input data may, for example, be used for marketing and/or product development.

Figure 3A:
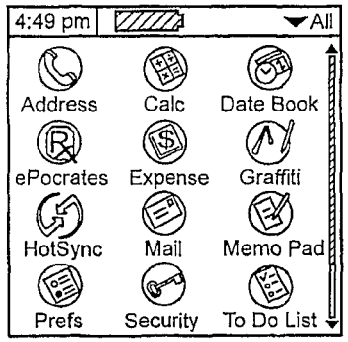
FIGS. 3A-3AJ illustrates a graphical user interface in accordance with an embodiment of the present invention.

An example of the present invention's application interface will now be discussed for the case where a physician is treating a patient in his examination room. Earlier in the day the physician may have synchronized his PDA with the server as discussed supra to obtain the latest revisions to the databases 228. The physician typically ascertains which insurance plan the patient belongs to by either looking at the patient's chart or by enquiring from the patient which plan he belongs to. At any point before, during or after the examination of the patient, the physician typically consults his/her PDA. FIG. 3A shows a typical start-up or main GUI of the PDA containing software according to the present invention. Most PDAs include an address book, calculator, to do list and a memo pad. In addition to the abovementioned applications, the PDA also includes an application capable of displaying interactive health care data. In this example the application is called ePocrates® qRx and is represented by the Rx icon. Furthermore, in this example the PDA used is a Palm V™ Connected Organizer from 3Com Inc, which uses a touchscreen, but it should be appreciated that any electronic device with similar capabilities could be used. By clicking on the ePocrates® qRx icon, a physician runs the application that displays the GUI shown in FIG. 3B.

Figure 3B:
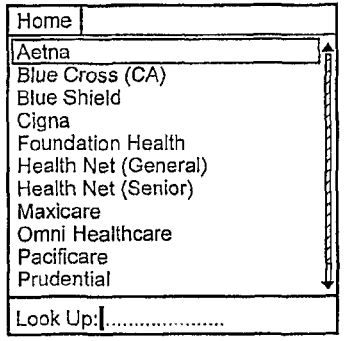

The GUI in FIG. 3B lists all possible health plans that a patient may belong to. The health plans listed are in this example, all the major health plans with which that physician contracts, such as for example Aetna®, Blue Cross® or Cigna®. Any regional or sub-grouping of a plan will also be displayed, for example plans that are State or employer specific. Lets say, in this example, the physician is informed by the patient that the patient contracts with the Cigna® heath plan. The physician then clicks on the line displaying Cigna®, displaying the GUI shown in FIG. 3C.

Figure 3C:
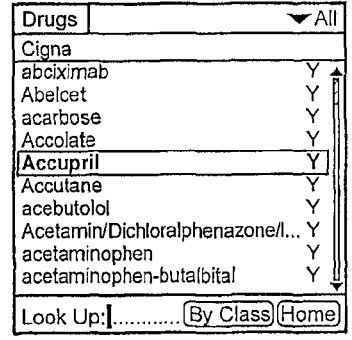

The GUI in FIG. 3C lists all medications or drugs available under the Cigna® plan. A letter next to each drug indicates the drug's status relative to the formulary. For example, Y means that particular drug is covered by the patient's health Plan (Cigna®). N means the drug is not on the formulary, G means the drug is on formulary but only in a generic form, PA means prior authorization is required, and P means the drug is preferred. Using this list the physician may quickly determine whether or not a particular drug is on formulary. By clicking on PA, a pop-up screen is displayed showing the process necessary to get authorization (not shown).

Figure 3D:
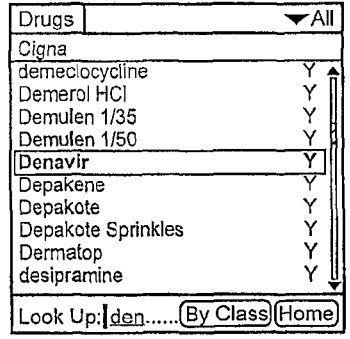

There are different ways to search for a specific drug. One way is using the up and down scroll buttons on the PDA, another way is using the arrows on the screen. The physician may also search for a particular drug by typing in at least part of the drug's name next to "Look Up", as shown in FIG. 3D.

Here the physician types in "den", the first three letters of the drug "Denavir", and the list automatically scrolls to all drugs beginning with the letters "den".

Figure 3E:
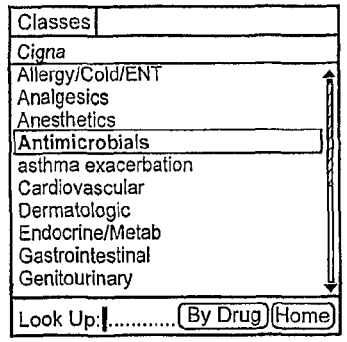

The physician may prefer to search for all drugs in a particular medical class. By clicking on the "By Class" button in the lower right hand corner of the GUI shown in FIGS. 3C and 3D, the physician displays a GUI listing drugs in medical classes, as shown in FIG. 3E.

Figure 3F:
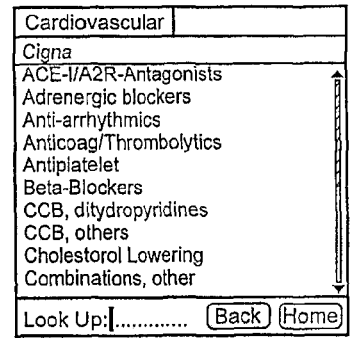

Let's say for example that the patient suffers from a cardiovascular complaint. By clicking on "cardiovascular" in FIG. 3E, the GUI shown in FIG. 3F is displayed, listing all medical sub-classes of cardiovascular drugs. In a similar manner, in FIG. 3F, the physician may click on all "Beta-Blockers" to be presented with a GUI, FIG. 3G, displaying a list of all Beta-Blocker drugs in the sub-class of cardiovascular drugs. This list now indicates the status of all Beta-Blocker drugs on the patient's health plan, in this case Cigna®.

Figure 3G:
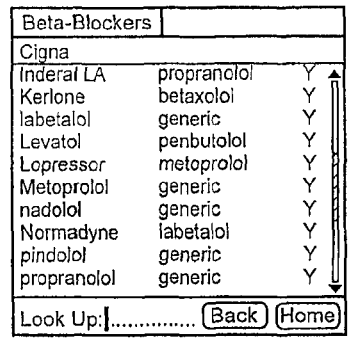
Figure 3H:
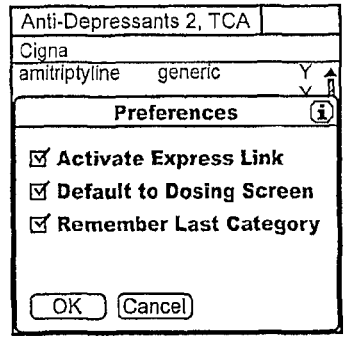

By clicking on a down arrow in the bottom left hand corner of a data entry frame (not shown) surrounding all the GUIs, the physician is presented with a menu (as shown in FIG. 3Z), from which he may click on "Options" and then "Preferences" (as shown in FIG. 3AF), displaying a list of the physician's preferences for this application as shown in FIG. 3H. Preferences may include for example, a setting that activates an express link that takes one directly from the previous screen to the screen that deals with that drug, a setting that defaults to a dosing screen, and a setting that remembers the last category. The physician can check any of the boxes associated with each preference setting and may save the preference setting by clicking on the "OK" button or may close the preference setting's GUI without saving the settings by clicking on the "Cancel" button.

Figure 3I:
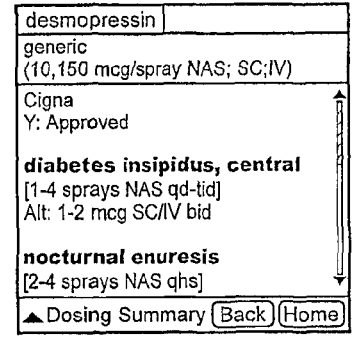

The physician may click on any drug name listed in FIG. 3C, 3D or 3G, for example, "desmopressin", to display clinical data about that drug as shown in FIG. 3I. This feature of the application links the formulary data with clinical data. (The dosing details GUI will be defaulted to if the preference setting for "Default to Dosing Screen" is checked, as shown in FIG. 3H.) Information supplied to the physician may include whether the drug is a generic, the different formulations in which the drug is available such as for example a 20 mg capsules, 40 mg capsules or 150 mcg spray or an intravenous drip (IV), typical dosage information, such as 20 mg PO BID (taken orally twice a day), and an indication on whether the drug is approved by the particular health plan. Dosage may include standard abbreviations such as for example IV meaning intravenous, IM meaning intramuscular, PV meaning per vagina, PR meaning per rectum, QD meaning once a day, BID meaning twice a day, TID meaning three times a day, QID meaning four times a day, QAM meaning every morning, QPM meaning every night, QHS meaning before sleep, and PRN meaning as needed. Additional information may also be displayed relating to dosing, the starting dose, the maximum dose and how one adjusts the dosage before terminating the prescription, such as for example with steroids one needs to gradually lower the dosage over time. Furthermore, additional indications other than the common indication may also be displayed, indicating the typical form the drug will take and the typical dosage for that condition. So for example, the same drug may be used to treat hypertension, hypertension with diuretics, and congestive heart failure, all with different dosing regimens. An example GUI for another drug is shown in FIG. 3J, this time for the drug "Accupril".

Figure 3J:
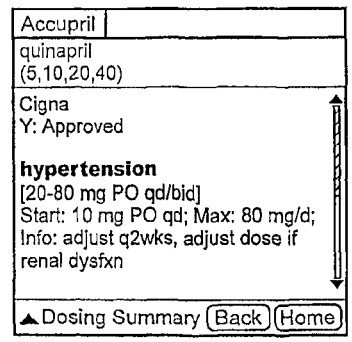
Figure 3K:
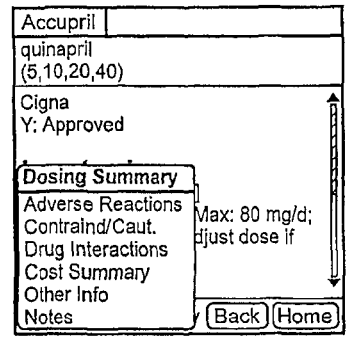
Figure 3L:
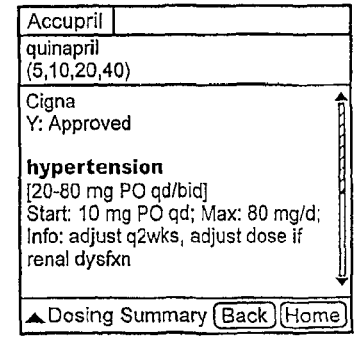

Should the physician desire other information about that drug, he may click on the up-arrow in the bottom left corner of the screen shown in FIG. 3J, displaying the GUI shown in FIG. 3K. As can be seen a small menu screen is displayed listing other drug topics such as "Adverse reactions", "Constraind/Caut." which is an abbreviation for contraindications or cautions, "Drug Interactions" with other drugs, "Cost Summary", "Other Info", or "Notes". By clicking elsewhere on the screen the pop-up screen is closed returning to the most recent screen, as shown in FIG. 3L.

If the physician clicks on "Adverse Reactions" in the GUI shown in FIG. 3K, the GUI for adverse reactions will be displayed, as shown in FIG. 3M. This GUI lists that particular drug's adverse reactions in groups, such as for example "Serious Reactions" or "Common Reactions". Reactions for this drug may include symptoms like dizziness or hepatoxicity.

If the physician clicks on "Constraind/Caut." in the GUI shown in FIG. 3K, the GUI for contraindications or cautions will be displayed, as shown in FIG. 3N. This GUI lists all known contraindications or cautions linked to that particular drug, such as for example that pregnant women should not use the drug.

If the physician clicks on "Drug Interactions" in the GUI shown in FIG. 3K, the GUI for drug interactions will be displayed, as shown in FIG. 3O. This GUI lists all known interactions between that particular drug and other drugs or classes of drugs, such as for example diuretic drugs. Clicking on any drug or class of drugs will display a pop-up screen displaying the nature of the interaction and the adjustments which are necessary (not shown).

If the physician clicks on "Cost Summary" in the GUI shown in FIG. 3K, the GUI for drug costs will be displayed, as shown in FIG. 3P. Drug costs may be displayed grouped into insurance co-payments by patients, average wholesale prices and/or retail prices from a particular pharmacy. FIG. 3Q shows the remainder of the GUI not displayed in FIG. 3P, indicating the different average wholesale prices for different strengths of the drug.

Older patients with fixed incomes often have a high monthly expenditure for medication. Physicians therefore need to be sensitive to their patient's drug costs. To assist the physician, retail prices could therefore also be displayed.

If the physician clicks on "Other Info" in the GUI shown in FIG. 3K, the GUI for other information will be displayed, as shown in FIG. 3R. Other information may include information about a drug's relation to pregnancy, lactation, metabolism, excretion, whether it is a substance controlled by the Drug Enforcement Agency, the manufacturer of the drug, that particular drug's medical class, and when the formulary for that health plan was last updated. By clicking on underlined links, small balloon GUIs are displayed. For example, clicking on "D" next to "Pregnancy" in FIG. 3R opens a GUI shown in FIG. 3S further explaining that the "Human studies . . . "; clicking on the question mark next to "Lactation" in FIG. 3R opens a GUI shown in FIG. 3T further explaining that the "Safety is unknown . . . "; or clicking on "not controlled" next to "DEA" in FIG. 3R opens a GUI shown in FIG. 3U further explaining that the "Drug is not subject . . . ".

If the physician clicks on "Notes" in the GUI shown in FIG. 3K, the GUI for notes taken by the physician for that particular drug will be displayed, as shown in FIG. 3V. The physician may enter anything he desires in this space which may be saved for later retrieval. Frequent note taking by the physician amasses vast amounts of data which make the PDA more valuable and indispensable to that physician and raises the switching costs. Furthermore, if desired, these notes may be uploaded to the server to be analyzed, as explained in relation to the tracking database supra. The physician can, for example, store information specific to his geographical setting, preferred route for administering the drug, experiences he has had with the drug, or news concerning the drug.

Using infrared beaming technology present on many PDAs, a physician may also beam notes he has taken to other PDAs. Pharmaceutical representatives can also beam additional into to the physician's PDA. The beaming process is accomplished as is illustrated in FIGS. 3Z and 3AB.

Furthermore, a physician may create new categories for drugs or information that he feels should be separated or grouped together. As shown in FIG. 3W, the physician enters a name for the new category and clicks the "OK" button to save the category or the "Cancel" button to exit to the last GUI without saving. An example of this may be where a physician creates a category that lists all his favorite drugs in a separate category called "My Drugs", as shown in FIG. 3W. This GUI may be accessed by clicking on a down arrow in the bottom left hand corner of a data entry frame (not shown) surrounding all the GUIs, the physician is presented with a menu (as shown in FIG. 3Z), from which he may click on "Drug" and then "Categorize". FIG. 3X illustrates the categories created. The categories may be renamed by clicking on the "Rename" button, or deleted by clicking on the "Delete" button. A new category may be created by clicking on the "New" button. The physician may exit to the last screen by clicking on the "OK" button.

As shown in FIG. 3Y a pop-up GUI will open where one may edit a category of drugs or view a category.

Drugs are approved by the Food and Drug Administration (FDA) for a specific indication, called an on-label indication. However, once a drug has been approved by the FDA, a physician may use it for other indications, called off-label indications. For example Prozac is used for depression, but it may also be used for bulimia. The FDA may not have approved the drug for bulimia even though it is in widespread use for that condition. However, whoever makes or vends the drug legally cannot currently promote the drug for treating Bulimia. The application on the PDA indicates off-label indications with an asterisk, next to the drug or treatment name.

FIG. 3AC illustrates edit functions which the user may use within the application.

A list of abbreviations is illustrated in FIG. 3AD. This GUI may be accessed by clicking on a down arrow in the bottom left hand corner of a data entry frame (not shown) surrounding all the GUIs, the physician is presented with a menu (as shown in FIG. 3Z), from which he may click on "Options" followed by "Abbreviations" as shown in FIG. 3AF. The preferences, disclaimer and about ePocrates GUIs may also be accessed via the options tab. The "About ePocrates" listing under the options tab, displays the GUI illustrated in FIG. 3AG, which displays information about the application. One may click on the "OK" button to exit the about ePocrates screen or one may click on the "Credits" button which will open the GUI illustrated in FIG. 3AH, setting out more information about the company and or application. FIG. 3AE illustrates a disclaimer screen that may be triggered to display when the application is launched or the screen if selected from the GUI illustrated in FIG. 3AF.

Another advanced feature of the present invention is that of the find function illustrated in FIGS. 3AI and 3AJ. Assume, for example, a patient is suffering from abdominal pain and after some tests it turns out that the patient has angioedema. By searching through a list of adverse reactions to the medications the patient is currently using, a physician may determine that the patient's condition is caused by other medication he is taking that in a small percentage of the cases causes angioedema. For a physician to know or look up all the possible side effects of every drug is impossible, especially for the less commonly used drugs. Using this function, the physician can search under angioedema and can cross reference the ailment against the medication the patient is taking. Referring to FIG. 3AI, a physician may enter the ailment which he has diagnosed. By clicking on the down arrow, the physician is able to select the database in which he would like to search, in this case the adverse reactions database. The physician may then initiate the search by clicking on the "ok" button or cancel the search by clicking on the "cancel" button. Should he click on the "ok" button, the search will start as indicated in FIG. 3AJ. A progress bas indicates how much longer the search will take. As evident from FIG. 3AJ, at least one drug, namely Floxin, has the adverse reaction of pruritis.

Furthermore, while the PDA is synchronizing, advertisements or other information may be displayed on the desktop computer's screen. Such advertisements are preferably downloaded the previous time that the PDA was synchronized, stored in the desktop computer's memory and displayed when the PDA is next synchronized. These advertisements or other information can support HTML and be interactive. Clicking on an advertisement will launch the browser and direct the user to a website selected by the message sponsor. The browser may alternatively automatically launch to a predetermined website rather than depending on the user to do so.

If physicians utilize the present invention, as set out above, health care insurers and PBMs will get a higher compliance with their formularies, ultimately reducing the cost of the medication. Physicians will also benefit, as they will have a higher compliance with formularies leading to less time wasted, lower expenses and if they participate in risk pooling, more revenue. Physicians will also benefit tremendously from the clinical and other data.

Patients may also benefit from receiving clinically efficacious and cost effective (ie. "covered by insurance" medication).

Interactive Messaging System

Another embodiment of the present invention comprises an interactive messaging system which provides physicians with timely and relevant information that is customized specifically for an individual physician or group of physicians. This information is presented to physicians in the form of messages that are downloaded and stored each time a physician performs a synchronization of the PDA. Physicians may view and interactively respond to these messages at their leisure. Messages may be customized to each physician's profile, enabling one-to-one marketing capabilities and content a physician may find relevant to his interests. The application which runs the interactive messaging system resides on the PDA. A set maximum amount of messages are stored at any one time on the PDA. The interactive messaging system launches at the end of the synchronization process, at a set time or each time a physician turns on the PDA. The physician will be able to read the messages at that time or choose to read them at a later time. If a physician chooses not to read messages at that time, the program will preferably return the user to the last open GUI on the PDA. If the physician chooses to read the messages, he or she may read through all unread messages. After the physician responds to each message, it is deleted. If the physician exits the interactive messaging system application without responding to the current message, that message will be treated as unread.

Between each synchronization session, the physician will preferably never have to view more than the set maximum amount of messages stored on the PDA.

Figure 4A:
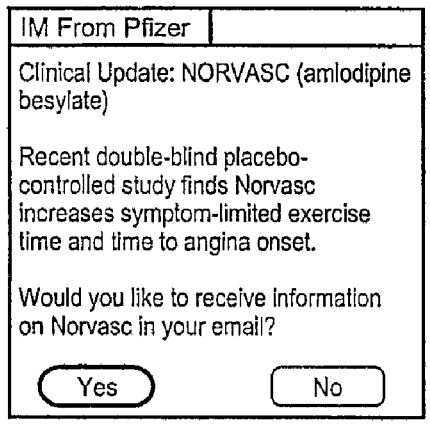
FIG. 4A-4D illustrates a second graphical user interface in accordance with another embodiment of the present invention.
Figure 4B:
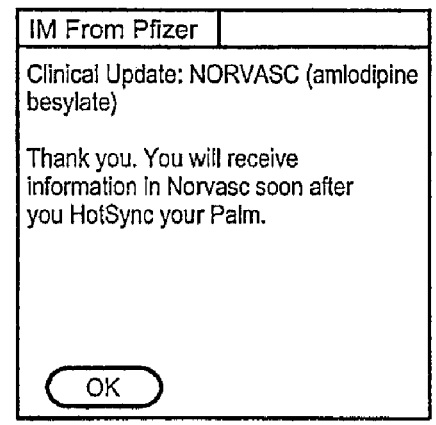
Figure 4C:
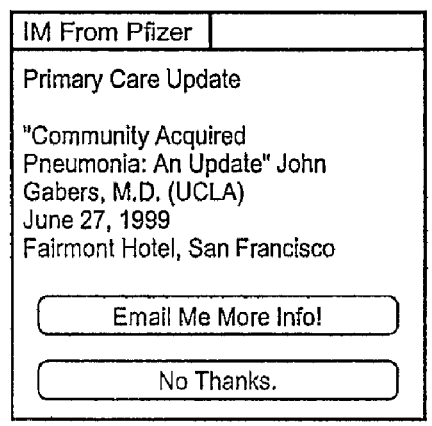
Figure 4D:
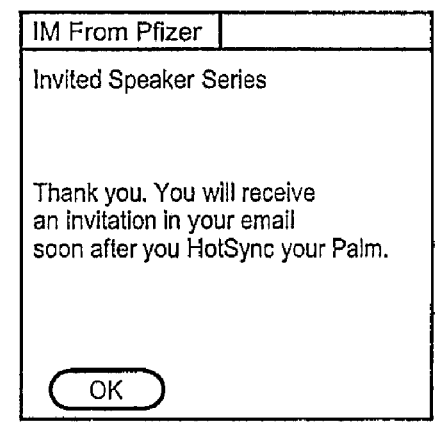

Messages preferably consist of text, buttons and/or graphics. Examples of such text GUIs are illustrated in FIG. 4A and FIG. 4C. Messages may also include questions, such as for example whether a physician would like further information on a certain topic. Possible responses may include Yes/no, email me/don't email me, or answers that the physician can select. The interactive messaging may support scrolling of messages, though single screen messages are preferable for effectiveness. If the physician responds in the negative, the message GUI will close and the interactive message will be deleted. If the physician responds in the positive, the response will be stored in another database on the PDA and uploaded to the server when the PDA is synchronized. Alternatively, both positive and negative responses could be recorded and uploaded to the server. FIGS. 4B and 4D illustrate the GUIs which may be displayed after the physician has affirmatively responded to the questions posed in GUIs shown in FIGS. 4A and 4C.

In the present embodiment, once a physician responds to the interactive message, the response cannot be changed. Other embodiments, of course, could allow the physician to change his response. Each message may also have an expiration date. If a message expires before a physician has read it, it will be automatically deleted from the PDA.

Messages can be specifically targeted to an individual physician or a group of physicians. Physicians may be identified by their practice areas, number of prescriptions written or even their Drug Enforcement Agency Number (DEA#), or Medical Education Number (ME#).

Any new messages sent since the last synchronization are automatically downloaded to the PDA each time the physician synchronizes the PDA if the set maximum amount of messages has not been met. At the same time, responses to old messages are uploaded to the server. Messages waiting in the queue on the server to be downloaded to the physician's PDA may be prioritized by expiration date, importance or urgency.

Examples include an alert concerning the removal of a medication from the market by the FDA, or an invitation to a lecture. Should the physician, for example, accept an invitation to a lecture an entry for that event will be entered into the physician's PDA Calender/Datebook and generate a positive response which would be uploaded to the server and forwarded to the message sponsor.

By utilizing the interactive messaging system, health care insurers, PBMs, pharmaceutical companies, CROs, managed care organizations, and others have a means of communicating directly with physicians.

Distribution

Figure 5:
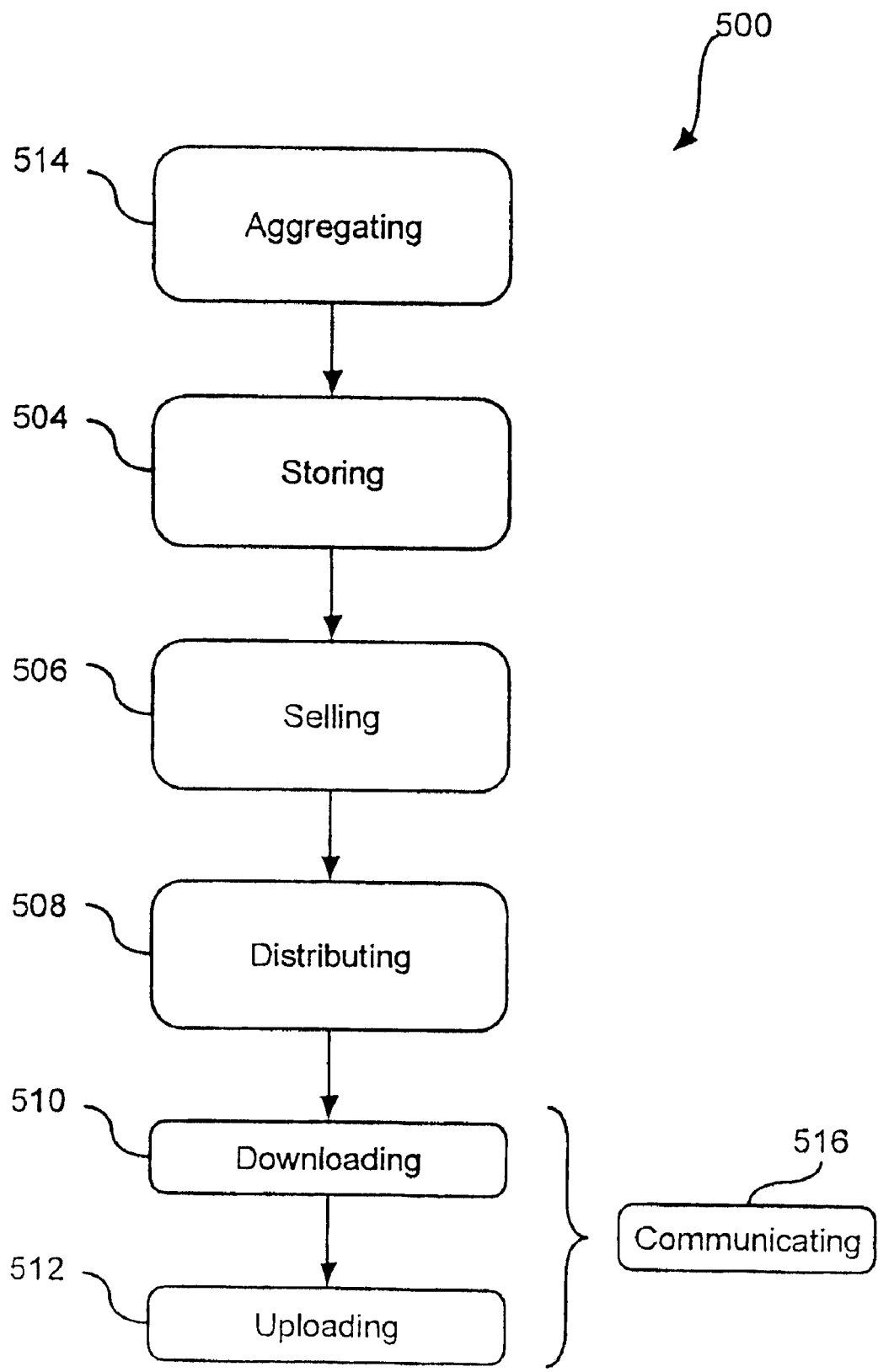
FIG. 5 illustrates a method of supplying industry specific data to a first party according to a preferred embodiment of the present invention.

FIG. 5 illustrates a method 500 for supplying industry specific data to a first party, such as a medical worker like a physician. As physicians are reluctant to pay for information technology, the present invention comprises a system and method for supplying industry specific data to physicians at no cost.

Industry specific data is aggregated 514 from multiple sources such as for example databases like PBM's formulary databases, Internet web sites, or other networks. The aggregated data is then stored 504 in a memory. The industry specific data may include pharmacopeia type information, clinical information, formularies, dosing information, co-payment information, drug pricing, adverse reaction information, drug-drug reaction information, contra-indication information, metabolism or excretion information, Drug Enforcement Agency schedules, drug trial information or criteria, lab results, pathology reports, x-ray reports, medical records, reference data, or pregnancy and lactation information.

Sponsorship rights are sold 506 to a second party to either pay for individual PDAs or to pay for the service of providing industry specific data to a first party. The second party may be health care industry companies such as health plans or pharmaceutical companies, medical device companies, Pharmacy Benefit Management companies, Contract Research Organizations, or managed care organizations. These other individuals or companies merely sponsor the distribution and service of the PDAs and preferably do not own the PDAs. The party who controls the updating and content of the PDA preferably retains ownership. The PDAs are then distributed 508 to the first party (the physician) either by the party who controls the updating and content of the PDA or by the second party (the pharmaceutical company). A preferred method is where the rights to sponsor a physician's PDA are sold 506 to a pharmaceutical company, who distributes 508 the PDA to the physician through its pharmaceutical representatives in the field. Finally the aggregated data is remotely communicated 516 to the PDAs as discussed supra. The content of the PDA's memory may be managed remotely which may include downloading 510 data or software to the PDA, or uploading 512 data from the PDA, as discussed supra in relation to interactive messaging. It should be appreciated that this system can be utilized to supply other individuals, such as for example stock brokers, with information specific to their industry.

The pharmaceutical companies obtain benefits for sponsoring the PDAs, namely: direct-to-physician marketing campaigns; representatives may be able to establish long-term positive relations with physicians by using the PDA as a door opener; representatives may obtain high value face time consulting with physicians; profile data may be gathered on usage and user profiles of the physicians using the tracking database discussed supra; the pharmaceutical company may obtain brand placement on the device; representatives may make follow-up visits to demonstrate new features/benefits; interactive messaging allows one-to-one marketing; desktop advertisements while synchronizing allow the pharmaceutical companies to directly market to their target audience; representatives may offer top physicians low-cost high-value accessory items; working with PBMs night help pharmaceutical companies in their pricing and contract negotiations; and displaying formularies to physicians at the point of care increases on formulary prescribing and renders the rest of their marketing campaign more effective where the pharmaceutical company has good formulary positioning.

The overall result for the pharmaceutical companies is a profitable marketing campaign allowing them to fully utilize their sales force and to use a new platform to provide physicians with information which will increase their role in the decision-making.

Benefits for PBMs include improved formulary compliance, increased mail order volume, and inexpensive and rapid updates which provide greater flexibility in contracting.

Patient, pharmacist, and regulatory frustrations may be eased and negative public sentiment and lobbying activities against formularies may be reduced by eliminating off-formulary prescriptions.

The method of distributing PDAs to physicians does not run afoul of the AMA ethical regulations because the PDA is not given, but merely lent, to the physician. Furthermore the PDA almost exclusively contains health care reference data that the physician can utilize in his or her practice. There is also little concern that pharmaceutical companies might have influence over physicians as the pharmaceutical companies do not control the content transmitted to the PDAs.

Other Embodiments

Reminder screens/GUIs may alert the physician to synchronize the PDA if he or she has not done so recently, especially in the case that responses to messages have not been uploaded for more than a set amount of time. The PDA may be used for additional applications, such as treatment pathways, on-line prescription ordering, script tracking and instant messaging.

An installer may be included in the system for downloading new programs or applications to the desktop computer in a compressed file format. Once downloaded, the physician opens the downloaded file, typically by double clicking on an associated icon for the downloaded file, which runs an install tool which places the new application files in an appropriate desktop PDA install directory. The files are then automatically installed on the PDA during the next synchronization session. If multiple users or physicians, with associated PDAs, are utilizing a single desktop computer, the installer will prompt the user to select the appropriate user.

A provider of the system or method may also offer its customers free e-mail, voice mail, and fax services. During the synchronization session, if the user has messages in any of their e-mail, voice mail, or fax "boxes", a message will be displayed on the desktop screen as part of this feature indicating the number of messages in each box. The user can select an appropriate portion of the desktop screen and go directly to a web page to review their messages.

An Internet browser capable of viewing and storing medical and other websites may also be included on the PDA. This allows the user to view content from the Internet off-line at their convenience.

An address book of the PDA may be preloaded with contact information for local hospitals, pharmacies, and physicians based on factors such as the physician's address or the region's population density.

Furthermore, the PDA may include an interactive trivia game. Every day, new industry specific questions, generally in a multiple choice format, will be posted on the server. A MAL-enabled download will download these questions to the PDA. The user can answer the questions which may be uploaded to the server during the next MAL-enabled synchronization session. Points for the game will be awarded for correct answers and speed in answering the questions, the highest scoring participants receiving a prize.

The user may also enter a term to be searched. During the next MAL-enabled synchronization session, this term will be uploaded and used to generate a database search, the results being downloaded during the following MAL-enabled synchronization session. Using a wireless network, real-time searches may also be conducted. The search term will be entered and sent over the wireless network to a server to initiate a query. The results will then be returned over the same network to the PDA.

The PDA can be used to facilitate clinical trials. Pharmaceutical and medical device companies, as well as contract research organizations, can use the PDA to communicate research protocols, inclusion/exclusion criteria, and research progress updates. This should facilitate patient enrollment and study completion. The PDA can also be used to recruit physicians to serve as principal investigators for the study.

Physicians generally need to remain current with medical advances. They do so through continuing medical education (CME) courses. The PDA can be used to deliver educational material as well as multiple choice exams demonstrating the physician's mastery of the new information. The content would be delivered and responses obtained in any of the manners mentioned supra.

Indicia of the sponsored entity such as the pharmaceutical companies logo, may also be placed on the PDA.

Various embodiments of the invention have been described. The descriptions are intended to be illustrative of the present invention. It will be apparent to one of skill in the art that modifications may be made to the invention as described without departing from the scope of the claims set out below.

We claim:

1. A method for distributing medical information stored on a computer system to an interactive health care data application on a physician's handheld computing device, the method comprising:
   at a server in the computer system:
      identifying a group of one or more physicians to receive customized medical information including educational materials, wherein the group of one or more physicians have a common medical practice area or industry specific interest, and the medical information is relevant to the medical practice area or industry specific interest;
      generating an interactive message comprising said customized medical information, multiple choice questions relating to the educational materials, and objects that the one or more physicians in the group can select to respond to the questions; and
      transmitting the interactive message from the computer system to one or more interactive health care data applications, wherein each interactive healthcare data application is running on a respective handheld computing device associated with a respective physician of the group of one or more physicians.

2. The method of claim 1, further comprising:
   prior to transmitting the interactive message to a respective handheld computing device, receiving, at the server, a signal from the respective handheld computing device, wherein the signal indicates an availability of the respective handheld computing device for receipt of the interactive message; and
   wherein the transmitting is performed automatically in response to receiving the signal from the respective handheld computing device.

3. The method of claim 2, wherein the receiving further comprises receiving, from the respective handheld computing device, an indication of an amount of interactive messages that are currently stored on the respective handheld computing device; and if the amount is above a maximum amount, storing the interactive messages on the server instead of transmitting the interactive messages to the respective handheld computing device.

4. The method of claim 1, wherein the identifying is based on information selected from the group consisting of: a practice area of each respective physician of the group of one or more physicians; a number of prescriptions written by each respective physician; a Drug Enforcement Agency number of each respective physician, a medical education number of each respective physician, and any combination of the aforementioned.

5. The method of claim 1, wherein the interactive message includes an interactive question directed to each respective physician of the group.

6. The method of claim 1, wherein the interactive message includes a question asking the respective one or more physicians of the group if the respective physician would like further information on a certain medical topic.

7. The method of claim 1, wherein the customized medical information includes information selected from the group consisting of: clinical information, drug-drug reaction information, contra-indication information, drug trial information, medical record data, clinical protocol information, and any combination of the aforementioned.

8. The method of claim 1, wherein the generating further comprises associating an expiration date with the interactive message, such that the interactive message expires after a predetermined time.

9. The method of claim 1, wherein the interactive message is configured to be automatically displayed to the respective physician of the group once downloaded to the respective handheld computing device.

10. The method of claim 1, further comprising prioritizing the interactive message by a category selected from the group consisting of: an expiration date, importance, and urgency.

11. The method of claim 1, further comprising:
   storing medical data in a database on the server; and
   communicating at least some of the medical data from the database to the respective handheld computing device in response to a connection signal received from the respective handheld computing device.

12. The method of claim 11, further comprising, before the storing, aggregating the medical data from multiple sources.

13. The method of claim 12, wherein the aggregating step further comprises collecting medical data from a group consisting of: formulary data, pharmacopeia data, and any combination of the aforementioned.

14. The method of claim 13, wherein the communicating the medical data further comprises:
   receiving a request for medical data from the respective handheld computing device; and
   responding to the request by sending at least a portion of the medical data to the respective handheld computing device.

15. The method of claim 1, wherein the objects include answers each respective physician of the group can select without typing text.

16. The method of claim 1, wherein the educational materials are continuing medical education materials and the multiple choice questions relate to the continuing medical education materials.

17. The method of claim 1, further comprising periodically, and without human intervention, communicating customized medical information between the server and the respective handheld computing device.

18. A computer readable storage medium, storing one or more programs for execution by one or more processors at a server system, the one or more programs storing instruction for distributing medical information stored on a computer system to an interactive health care data application on a physician's handheld computing device, the one or more programs comprising:
   instructions for identifying a group of one or more physicians to receive customized medical information including educational materials, wherein the group of one or more physicians have a common medical practice area or industry specific interest and the medical information is relevant to the medical practice area or industry specific interest;
   instructions for generating an interactive message comprising said customized medical information, multiple choice questions relating to the educational materials, and objects that the one or more physicians in the group can select to respond to the questions; and instructions for transmitting the interactive message from the computer system to one or more interactive health care data application, wherein each interactive healthcare data application is running on a respective handheld computing device associated with a respective physician of the group of one or more physicians.

19. The computer readable storage medium of claim 18, further comprising:

instructions for, prior to transmitting the interactive message to a respective handheld computing device, receiving, at the server, a signal from the respective handheld computing device, wherein the signal indicates an availability of the respective handheld computing device for receipt of the interactive message; and wherein the transmitting is performed automatically in response to receiving the signal from the respective handheld computing device.

20. The computer readable storage medium of claim 19, wherein the instructions for receiving further comprises receiving, from the respective handheld computing device, an indication of an amount of interactive messages that are currently stored on the respective handheld computing device; and if the amount is above a maximum amount, instructions for storing the interactive messages on the server instead of transmitting the interactive messages to the respective handheld computing device.

21. The computer readable storage medium of claim 18, wherein the instructions for identifying is based on information selected from the group consisting of a practice area of each respective physician of the group of one or more physicians; a number of prescriptions written by each respective physician; a Drug Enforcement Agency number of each respective physician, a medical education number of each respective physician, and any combination of the aforementioned.

22. The computer readable storage medium of claim 18, wherein the customized medical information includes information selected from the group consisting of clinical information, drug-drug reaction information, contra-indication information, drug trial information, medical record data, clinical protocol information, and any combination of the aforementioned.

23. The computer readable storage medium of claim 18, wherein the instructions for generating further comprises associating an expiration date with the interactive message, such that the interactive message expires after a predetermined time.

24. The computer readable storage medium of claim 18, wherein the interactive message is configured to be automatically displayed to the respective physician of the group once downloaded to the respective handheld computing device.

25. The computer readable storage medium of claim 18, further comprising instructions for prioritizing the interactive message by a category selected from the group consisting of: an expiration date, importance, and urgency.

26. The computer readable storage medium of claim 18, further comprising:

instructions for storing medical data in a database on the server; and instructions for communicating at least some of the medical data from the database to the respective handheld computing device in response to a connection signal received from the respective handheld computing device.

27. The computer readable storage medium of claim 26, further comprising, instructions for aggregating the medical data from multiple sources.

28. The computer readable storage medium of claim 27, wherein the instructions for aggregating step further comprises instructions for collecting medical data from a group consisting of: formulary data, pharmacopeia data, and any combination of the aforementioned.

29. The computer readable storage medium of claim 18, wherein the educational materials are continuing medical education materials and the multiple choice questions relate to the continuing medical education materials.

30. The computer readable storage medium of claim 18, further comprising instructions for periodically, and without human intervention, communicating customized medical information between the server and the respective handheld computing device.

* * * * *

UNITED STATES PATENT AND TRADEMARK OFFICE
CERTIFICATE OF CORRECTION

PATENT NO. : 7,856,365 B2  Page 1 of 1
APPLICATION NO. : 12/332557
DATED : December 21, 2010
INVENTOR(S) : Richard Alan Fiedotin et al.

It is certified that error appears in the above-identified patent and that said Letters Patent is hereby corrected as shown below:

On the Title Page, under Related U.S. Application Data, Item (63), please insert -- Continuation of application No. 09/487,932, filed on January 20, 2000, now issued patent 7,509,263 issued March 24, 2009 --

Column 1, line 5, insert -- and is a continuation of -- after the words "claims priority to"

Signed and Sealed this
First Day of March, 2011

David J. Kappos
*Director of the United States Patent and Trademark Office*